US012391735B2

(12) United States Patent
Zhu et al.

(10) Patent No.: US 12,391,735 B2
(45) Date of Patent: Aug. 19, 2025

(54) POLYPEPTIDE HAVING EFFECT OF INHIBITING PROLIFERATION OF LEUKEMIA CELLS

(71) Applicant: NANJING FENGRUI BIOTECHNOLOGY CO., LTD, Nanjing (CN)

(72) Inventors: Jiang Zhu, Nanjing (CN); An Zhong, Nanjing (CN); Meiqi Lv, Nanjing (CN)

( * ) Notice: Subject to any disclaimer, the term of this patent is extended or adjusted under 35 U.S.C. 154(b) by 77 days.

(21) Appl. No.: 17/299,292

(22) PCT Filed: Mar. 7, 2019

(86) PCT No.: PCT/CN2019/077271
§ 371 (c)(1),
(2) Date: Jun. 2, 2021

(87) PCT Pub. No.: WO2020/147176
PCT Pub. Date: Jul. 23, 2020

(65) Prior Publication Data
US 2025/0084138 A1    Mar. 13, 2025

(30) Foreign Application Priority Data
Jan. 15, 2019   (CN) .......................... 201910036210.9

(51) Int. Cl.
| C07K 14/47 | (2006.01) |
| A61P 35/02 | (2006.01) |
| C07K 1/06  | (2006.01) |
| C07K 1/16  | (2006.01) |
| A61K 38/00 | (2006.01) |

(52) U.S. Cl.
CPC .......... *C07K 14/4703* (2013.01); *A61P 35/02* (2018.01); *C07K 1/061* (2013.01); *C07K 1/16* (2013.01); *A61K 38/00* (2013.01)

(58) Field of Classification Search
CPC ........................... C07K 14/4703; C07K 1/061
See application file for complete search history.

(56) References Cited

FOREIGN PATENT DOCUMENTS
WO    2008021290 A    2/2008

OTHER PUBLICATIONS

Gas2, partial *Homo sapiens* GenBank: CAG29281.1 [online] Accessed Feb. 10, 2025 (Year: 2016) (Year: 2016).*
ISR of PCT/CN2019/077271.

* cited by examiner

*Primary Examiner* — Lianko G Garyu
*Assistant Examiner* — David Paul Bowles
(74) *Attorney, Agent, or Firm* — Hemisphere Law, PLLC; Zhigang Ma

(57) ABSTRACT

The present disclosure discloses a polypeptide having an effect of inhibiting the proliferation of leukemia cells, and particularly relates to use of the polypeptide in a drug for treating leukemia. The polypeptide consists of 37 amino acids, with the amino acid sequence thereof being Lys-Glu-Ser-Met-Asp-Ala-Asn-Lys-Pro-Thr-Lys-Asn-Leu-Pro-Leu-Lys-Lys-Ile-Pro-Cys-Lys-Thr-Ser-Ala-Pro-Ser-Gln-Ser-Phe-Phe-Ala-Arg-Asp-Asn-Thr-Ala-Asn, and the N-terminus of the polypeptide being conjugated with myristate. The polypeptide prepared by the present disclosure can enter the leukemia cells by conjugating with the myristic acid, thereby achieving the effect of inhibiting the proliferation of the leukemic cells.

2 Claims, No Drawings
Specification includes a Sequence Listing.

SEQUENCE LISTING

<160> NUMBER OF SEQ ID NOS: 1

<210> SEQ ID NO 1
<211> LENGTH: 37
<212> TYPE: PRT
<213> ORGANISM: Artificial Sequence
<220> FEATURE:
<223> OTHER INFORMATION: inhibiting the proliferation of leukemia cells polypeptide

<400> SEQUENCE: 1

Lys Glu Ser Met Asp Ala Asn Lys Pro Thr Lys Asn Leu Pro Leu Lys
1               5                   10                  15

Lys Ile Pro Cys Lys Thr Ser Ala Pro Ser Gln Ser Phe Phe Ala Arg
            20                  25                  30

Asp Asn Thr Ala Asn
        35

POLYPEPTIDE HAVING EFFECT OF INHIBITING PROLIFERATION OF LEUKEMIA CELLS

REFERENCE TO SEQUENCE LISTING

The substitute sequence listing is submitted as an ASCII formatted text filed via EFS-Web, with a file name of "Substitute_Sequence_Listing_97-1562-USUTIL.TXT", a creation date of Nov. 10, 2023, and a size of 776 bytes. The substitute sequence Listing filed via EFS-Web is a part of the specification and is incorporated in its entirety by reference herein.

TECHNICAL FIELD

The present disclosure belongs to the technical field of polypeptide drugs in biochemistry, and particularly relates to use of a polypeptide in a drug for treating leukemia.

BACKGROUND

Leukemia is a malignant tumor of hematopoietic stem cells. Clinically, leukemia is classified according to the degree of urgency of its incidence and pathological cells. Because the onset classification and prognosis stratification of leukemia are relatively complicated, it is necessary to formulate a comprehensive therapeutic regimen. In recent years, with the development of medical technology, a considerable number of patients can be cured, but some people still cannot be treated or suffer from diseases and pains due to drug resistance to therapeutic agents, and side effects and prognosis of the treatment. Chemotherapy drugs can only cure several types of leukemia, while the treatment of other types of leukemia still face many problems. For example, the acute myeloid leukemia (AML) and the acute T-cell lymphoblast leukemia (T-ALL) currently have no corresponding targeted drugs, and the chemotherapy effects on them are also very undesirable, so it is urgent to find novel treatment means.

Schneider treated NIH-3T3 (mouse fibroblasts) with a serum starvation method, and identified a group of specific and highly expressed genes, which were called growth-arrest specific genes (growth-specific inhibitory genes), and GAS2 was one member of the group.

It has been reported in literatures that GAS2 is abnormally expressed in various malignant hematological tumors and colon cancers, and targeting colon cancer cells and BCR-ABL$^+$ hematopoietic cells both have the effect of effectively inhibiting their proliferation, which indicates that GAS2 has the function of promoting/maintaining the proliferation of tumor cells. GAS2 binds to Calpain2 (calpain) mainly through its N-terminus, and its C-terminus plays the role of inhibiting the activity of calpain2 (calpain), thereby promoting the proliferation of tumor cells.

The truncated mutant GAS2Δ171-313 of GAS2 can also bind to Calpain2 (calpain), but it has no function of inhibiting the activity of Calpain2 (calpain) because of the absence of the C-terminus, so that it is a dominant negative mutant of GAS2 (GAS2DN). However, due to the existence of Calpain2 inside the cells, exogenous GAS2DN cannot penetrate the cell membranes and enter the cells to bind with Calpain2 (calpain).

Many research have shown that GAS2 (growth-arrest-specific 2) is abnormally highly expressed in various leukemias, and it has also be found that GAS2 is a novel regulatory factor for maintaining CD34$^+$ cells of CML, suggesting that targeting GAS2 may improve the treatment of various types of leukemias, and may also help for clearance of leukemia stem/progenitor cells. The results have been published (Zhou X, PloS One, 2014; 9: e86195; Sun L, Acta Biochim Biophys Sin (Shanghai), 2015; 47:795; Huang W, Oncotarget. 2017; 8:50629.).

The research also has found that both RNA interference and expression of GAS2DN can enhance the IM sensitivity of the CML cell line K562, suggesting that targeting GAS2 may enhance the chemotherapy sensitivity of the leukemic cells.

SUMMARY

In order to solve the above problems, the present disclosure develops a key polypeptide that plays a role of specifically binding to Calpain2 (calpain) in GAS2DN, determines a GAS2-like small peptide sequence, and provides a polypeptide having an effect of inhibiting the proliferation of leukemia cells, enables it to have the function of mimicking the GAS2DN protein and to serve as a GAS2 inhibitor to obtain therapeutic effects for leukemia patients.

Provided is a polypeptide having an effect of inhibiting the proliferation of leukemia cells, wherein the polypeptide consists of 37 amino acids, with the amino acid sequence thereof being:

Lys-Glu-Ser-Met-Asp-Ala-Asn-Lys-Pro-Thr-Lys-Asn-Leu-Pro-Leu-Lys-Lys-Ile-Pro-Cys-Lys-Thr-Ser-Ala-Pro-Ser-Gln-Ser-Phe-Phe-Ala-Arg-Asp-Asn-Thr-Ala-Asn (SEQ ID NO: 1).

The N-terminus of the polypeptide is connected with myristate, and enters the leukemia cells through modification with the myristate, thereby inhibiting the proliferation of the leukemia cells and being used for preparing a drug for treating leukemia.

Provided is a method for preparing the polypeptide according to claim 1, including the steps of:

1) Synthesis of Polypeptide
   a. pouring a resin Fmoc-Asn (trt) wang Resin into a reaction column, adding with DCM for soaking, and then suction-drying;
   b. adding proper amount of a deprotection solution, introducing nitrogen, stirring by agitation, and then suction-drying;
   c. adding proper amount of DMF into the glass reaction column, introducing nitrogen, stirring by agitation, and then suction-drying;
   d. adding a mixed amino acid solution or a protected amino acid and HBTU into the reaction column, then adding NMM, introducing nitrogen, stirring by agitation, and then suction-drying;
   e. adding proper amount of DMF for washing, introducing nitrogen, stirring by agitation, and then suction-drying to obtain granular substances;
   f. taking proper amount of the granular substances into a small test tube, adding each two drops of solutions A, B and C of a Kaiser test reagent, putting into a dry heater for heating, wherein if the color of the solution is yellowish and the granular substances are colorless and transparent, it is determined that the reaction is complete, and then repeating the above steps b-e to connect the next amino acid, until the last amino acid is connected with the myristate;
   g. adding proper amount of methanol into the reaction column after completion of the step f), agitating with nitrogen and then suction-drying, then adding proper amount of DCM, agitating with nitrogen and then suction-drying to obtain a synthetic polypeptide resin, loading it into a suitable vessel, and placing into a vacuum dryer for vacuum drying;

2) Cleavage of Polypeptide adding a polypeptide cleaving solution into the polypeptide resin, and placing and shaking in an environment with a constant temperature; then filtering, adding anhydrous ethyl ether into the filtrate, and stirring to precipitate a white solid; adding anhydrous ethyl ether into the white solid, centrifuging and washing, and vacuum drying to obtain white powder as the crude product of polypeptide;

3) Purification of Polypeptide taking proper amount of the crude product of polypeptide, adding with pure water and ACN for ultrasonic dissolution, filtering with a filter membrane, and then taking the filtrate; performing gradient detection analysis of the filtrate by a high performance liquid chromatograph on a normal-phase chromatographic column; adsorbing and eluting with a preparative chromatographic column to collect fractions; detecting the collected fractions, and freeze-drying the fractions with qualified purity to obtain a purified polypeptide.

Further, the deprotection solution is formulated from 20% hexahydropyridine and 80% DMF.

Further, the protected amino acid is a protected amino acid in a Fmoc-Aa-oh form, and the mixed amino acid solution is prepared by dissolving the protected amino acid in DMF.

Further, the solution A of the Kaiser test reagent is 80% phenol and 20% absolute ethanol, the solution B is distilled pyridine, and the solution C is 5 g ninhydrin and 100 ML absolute ethanol.

Further, the constituent components of the polypeptide cleaving solution is 87.5% TFA, 5% thioanisole, 2.5% phenol, 2.5% EDT, and 2.5% H2O.

Further, the step 3) purification of polypeptide is as follows:

preparation conditions:
wavelength: 220 nm
flow rate: 0.5-1.5 ml/min
Preparation column: Gemini-NX™ C18 reverse phase column (5 μm 110 Å, 4.6*250 mm column)
mobile phase: liquid A: 0.1% Trifluoroacetic in 100% Acetonitrile
liquid B: 0.1% Trifluoroacetic in 100% Water a) weighing proper amount of the crude product of polypeptide into a beaker, adding with pure water and ACN for ultrasonic dissolution, and filtering with a 0.45μ filter membrane after complete dissolution;
b) taking a small amount of the crude product of polypeptide into a centrifuge tube, ultrasonically dissolving with pure water until clarification, filtering, and detecting and analyzing with a gradient of 10-100%;
c) under the preparation conditions, equilibrating the instrument for about 6 minutes and then stopping all pumps, injecting the filtrate obtained through in the filtering in the step a) with an injection valve, first performing the gradient of 30-90% for 20 min, and then performing the gradient of 100-0% to collect fractions; and
d) detecting the collected fractions, and freeze-drying the fractions with qualified purity to obtain the purified polypeptide.

Beneficial effects: (1) the polypeptide prepared by the present disclosure has the inhibition function of inhibiting a GAS2DN protein, and can play a role in inhibiting GAS2, thereby playing a role in inhibiting the proliferation of the leukemia cells. However, since GAS2DN cannot penetrate the cell membranes and enter the cells, even if it has the function of inhibiting the proliferation of the leukemia cells, it cannot achieve the effect of inhibiting the proliferation of the leukemia cells. However, the polypeptide prepared by the present disclosure can enter the leukemia cells by connecting with myristate, so as to achieve the effect of inhibiting the proliferation of the leukemia cells. (2) The polypeptide prepared by the present disclosure has the function of inhibiting the proliferation of the leukemia cells, and meanwhile has no inhibitory effect on normal cells, so that a novel targeted therapeutic drug for treating leukemia can be developed by taking the polypeptide as the core component, thereby providing a brand-new treatment mode to reduce side effects, relieve the pain of patients and improve the cure rate and survival rate of leukemia. Especially for some leukemia subtypes, such as the acute T-lymphocyte leukemia cell line (T-All) and the acute myeloid leukemia cell line (AML), currently the chemotherapy effect is not good, and there is no suitable targeted drug. The polypeptide of the present disclosure can effectively inhibit the above two leukemia cells, suggesting that if a novel targeted therapeutic drug for treating leukemia is developed with the polypeptide as the core component, it is possible to fill the blank of targeted therapeutic drugs in these fields of leukemia treatment. (3) It is found by research that both RNA interference and expression of GAS2DN can enhance the IM sensitivity of the CML cell line K562, suggesting that targeting GAS2 may enhance the chemotherapy sensitivity of the leukemia cells. Therefore, the novel targeted therapeutic drug for treating leukemia developed with the polypeptide being the core component can be used in combination with a chemotherapy drug to enhance the therapeutic effect.

DESCRIPTION OF THE EMBODIMENTS

An objective of the present disclosure is to develop a key polypeptide in GAS2DN, determines a GAS2-like small peptide sequence, and provides a polypeptide having an effect of inhibiting the proliferation of leukemic cells, enables it to have the function of mimicking the GAS2DN protein and to serve as a GAS2 inhibitor to obtain therapeutic effects for leukemia patients.

The polypeptide of the present disclosure consists of 37 amino acids, with the amino acid sequence of the polypeptide being:

Lys-Glu-Ser-Met-Asp-Ala-Asn-Lys-Pro-Thr-Lys-Asn-Leu-Pro-Leu-Lys-Lys-Ile-Pro-Cys-Lys-Thr-Ser-Ala-Pro-Ser-Gln-Ser-Phe-Phe-Ala-Arg-Asp-Asn-Thr-Ala-Asn (SEQ ID NO: 1).

The N-terminus of the polypeptide is modified with myristic acid, and the polypeptide can enter cells to exert its inhibiting function by modification with myristate, thereby inhibiting the proliferation of the leukemia cells.

Example 1

Method for Preparing the Polypeptide:
Raw Materials and Formulation of Required Reagents
protected amino acids: various amino acids contained in the polypeptide are prepared into protected amino acids in a Fmoc-Aa-oh foam.
mixed amino acid solution: 1 mmol of each of the aforementioned various protected amino acids was weighed and dissolved in 63.4 ml of a DMF solution to formulate a 0.3 mmol/ml mixed amino acid solution for later use.

starting resin: Fmoc-Asn (trt) wang Resin.
condensing agent and organic base: HBTU, NMM.
solvents: DMF, DCM, methanol, and hexahydropyridine.
formulation of the Kaiser test reagent:
solution A: 80% phenol+20% absolute ethanol
solution B: redistilled pyridine
solution C: 5 g ninhydrin+100 ML absolute ethanol
formulation of deprotection solution:
20% hexahydropyridine+80% DMF
formulation of polypeptide cleavage solution:
87.5% TFA+5% thioanisole+2.5% phenol+2.5% EDT+2.5% H2O 1) Synthesis of Polypeptide
   a. resin swelling: the resin Fmoc-Asn (trt) wang Resin was weighed and poured into a glass reaction column, added with DCM for soaking for 30 minutes, and then suction-dried;
   b. deprotection: the glass reaction column was added with proper amount of the deprotection solution, introduced with nitrogen, stirred by agitation for 30 minutes, and suction-dried.
   c. deprotection washing: the glass reaction column was added with proper amount of DMF, agitated with nitrogen for 2 minutes, and suction-dried, and these operations were repeated for 6 times.
   d. feeding: the mixed amino acid solution at the amount of 3 times the molar weight of the resin or the same amount of the protected amino acids and HBTU at the amount of 2.85 times the molar weight of the resin, were weighed into the glass reaction column, then added with NMM at the amount of 6 times the molar weight of the resin, introduced with nitrogen, and stirred by agitation for 30 minutes.
   e. washing after reaction: the solution in the glass reaction column was suction-dried, added with proper amount of DMF for washing, agitated with nitrogen for 2 minutes, and suction-dried, and these operations were repeated for 3 times to obtain granular substances.
   f. detection: proper amount (10-20 particles) of the granular substances was taken into a small test tube, and added with each two drops of solutions A, B and C. It was put into a dry heater and heated for 3 minutes (110° C.).

After it was taken out, if the solution is presented as blue and the granular substance was mottled and opaque, the reaction was incomplete and needed to be reacted again;

If the color of the solution was yellowish and the granular substances were colorless and transparent, it was determined that the reaction was complete and the next amino acid could be connected. Specific steps were conducted by repeating the above five steps b-f until the last amino acid was connected.

h. washing and drying after completion of synthesis: after the connection between the last amino acid and myristic acid was completed and passed the detection, the glass reaction column was suction-dried, added with proper amount of methanol, agitated with nitrogen for 2 minutes, suction-dried, then added with proper amount of DCM, agitated with nitrogen for 2 minutes, and suction-dried, and these operations were repeated for 3 times. At last, the glass reaction column was added with proper amount of methanol, agitated with nitrogen for 2 minutes, and suction-dried, and these operations were repeated for 2 times to obtain a polypeptide resin, which was charged into a suitable vessel and placed into a vacuum dryer for vacuum drying for 12 hours for later cleavage.

2) Cleavage of Polypeptide
   Cleavage: the dried polypeptide resin was charged into a suitable round-bottom flask, added with proper amount of a formulated polypeptide cleavage solution (1 g/10 ml), and placed into a constant-temperature shaker for shaking at a constant temperature of 25° C. for 2 hours.
   Filtering: the undissolved polypeptide resin was filtered off with a 50 ml sand core funnel, then the filtrate was poured into a 100 ml centrifuge tube, and added with anhydrous ethyl ether at the amount of 6-8 times the volume of the resin under stirring, so as to obtain a precipitated white solid as the crude product of the desired polypeptide.
   Washing: the centrifuge tube was sealed, put into a centrifuge for centrifuging at the speed of 4,000 rpm (revolutions per minute) for 3 minutes, and then taken out, the supernatant was discarded, the centrifuge tube was then added with anhydrous ethyl ether, stirred evenly with a glass rod, and centrifuged again; operations and washing were repeated as such for 5 times.
   Drying: after washed for 5 times, the white solid was put into a vacuum dryer for vacuum drying for 24 hours. The finally obtained white powder was the crude product of the desired polypeptide, which was weighed and to be purified.

3) Purification of Polypeptide
   preparation conditions:
   instruments: high performance liquid chromatograph equipped with an ultraviolet detector
   wavelength: 220 nm
   flow rate: 1.0 ml/min
   Preparation column: Gemini-NX™ C18 reverse phase column (5 μm 110 Å, 4.6*250 mm column)
   mobile phase: liquid A: 0.1% Trifluoroacetic in 100% Acetonitrile
   liquid B: 0.1% Trifluoroacetic in 100% Water

|  | A | B |
|---|---|---|
| 0.01 min | 30% | 70% |
| 25 min | 90% | 10% |
| 25.1 min | 100% | 0% |
| 30 min |  | STOP |

Crude Analysis:
   a small amount of the crude product of polypeptide was taken into a 0.5 ml centrifuge tube, and dissolved with pure water until clarification, filtered and injected, and analysed with the gradient of 10-100%.

Separation and Purification:
a. Dissolution
   200 mg of the crude product of polypeptide was weighed into a 10 ml beaker, added with 7.5 ml pure water and 2.5 ml ACN for ultrasonic dissolution, and filtered with a 0.45μ filter membrane after complete dissolution.

b. Preparation
   The instruments were equilibrated with the preparation conditions by high performance liquid chromatograph (HPLC) for about 6 minutes, then all pumps were stopped, the filtrate obtained through filtering in the step a) was injected with an injection valve, the preparation gradient was run, first the gradient of 30-90% was executed for 20 min, and then the gradient of 100-0% was executed to collect fractions. After collection was completed, the pump was stopped. The collected fractions were checked for the purity thereof on an analytical instrument, and the fractions with qualified purity were freeze-dried.

c. Freeze Drying

The collected fractions were subjected to rotary evaporation of the organic solvent contained in the solution by a rotary evaporator, and then loaded onto a freeze dryer for freeze drying.

d. Weighing and Detecting

Two days after freeze-drying, the freeze dryer was open, a weighed weight was taken out and charged into a boutique tube, sent for QC detection, and put in storage when it is qualified upon detection.

Example 2

Experimental data was utilized to prove that the polypeptide of the present disclosure has the effect of inhibiting the proliferation of the leukemia cells.

The selected experimental cells were:

K562 cells of human chronic myeloid leukemia cell line (CML);

Jurkat cells of acute T lymphocyte leukemia cell line (T-ALL);

THP-1 cells of acute myeloid leukemia cell line (AML);

Baf-3 cells of normal mouse hematopoietic cells (mIL-3 dependent).

This experiment was grouped into a normal control group, a polypeptide control group, and an experimental polypeptide group.

Firstly, the polypeptide of the present disclosure was co-incubated with $5*10^3$ (marked as the third power of 10) leukemia tumor cells for 38 h, and the proliferation speed of the cells was detected by two methods of detecting proliferation of the cells (CCK-8) and cell counting, so as to observe the inhibitory effect of the polypeptide on the tumor cells.

Secondly, the polypeptide was co-incubated with the cells for 24 h, and then collected again, counted, and cultured with drug addition for 38 h, and then detected for the proliferation rate of the cells (CCK-8).

Thirdly, we used normal mouse hematopoietic cells to carry out the same experiment as the above to observe the effect of the polypeptide on normal cells.

Each group included one blank (Control), one control peptide (C-p), and three target peptides (P-t, taking an average as the result)

(1) K562 Cells Co-Incubated with the Polypeptide for 38 h/24+38 h

The First Experiment

TABLE 2.1.A

K562 cells co-incubated with
10 uM of the polypeptide for 38 h (%)

| Grouping | Cell survival rate (%) | Cell count (%) |
|---|---|---|
| Control | 100.00 ± 4.26 | 100.00 ± 5.82 |
| C-p | 91.23 ± 7.23 | 101.22 ± 13.21 |
| P-t | 83.43 ± 6.39** | 90.22 ± 28.17 |

TABLE 2.1.B

K562 cells co-incubated with
10 uM of the polypeptide for 24 + 38 h (%)

| Grouping | Cell survival rate (%) | Cell count (%) |
|---|---|---|
| Control | 100.00 ± 9.86 | 100.00 |
| C-p | 83.14 ± 2.99 | 89.46 |
| P-t | 90.11 ± 4.44 | 66.95 |

TABLE 2.1.C

K562 cells co-incubated with
15 uM of the polypeptide for 38 h (%)

| Grouping Cell | survival rate (%) | Cell count (%) |
|---|---|---|
| Control | 100.00 ± 9.16 | 100.00 |
| C-p | 88.34 ± 4.43 | 90.81 |
| P-t | 78.99 ± 3.30* | 69.55 |

The Second Experiment

TABLE 21.D

K562 cells co-incubated with
15 uM of the polypeptide for 38 h (%)

| Grouping | Cell survival rate (%) | Cell count (%) |
|---|---|---|
| Control | 100.00 ± 4.00 | 100.00 |
| C-p | 92.96 ± 2.83 | 81.76 |
| P-t | 81.44 ± 2.40* | 80.00 |

TABLE 2.1.E

K562 cells co-incubated with 15 uM of the
polypeptide for 24 + 38 h (%)

| Grouping | Cell survival rate (%) | Cell count (%) |
|---|---|---|
| Control | 100.00 ± 2.45 | 100.00 |
| C-p | 102.06 ± 3.45 | 91.90 |
| P-t | 77.39 ± 3.12* | 70.09 |

(2) Jurkat Cells Co-Incubated with the Polypeptide for 38 h/24+38 h

The First Experiment

TABLE 2.2.A

Jurkat cells co-incubated with 10 uM of the
polypeptide for 38 h (%)

| Grouping | Cell survival rate (%) | Cell count (%) |
|---|---|---|
| Control | 100.00 ± 4.01 | 100.00 |
| C-p | 118.91 ± 3.28 | 91.67 |
| P-t | 78.26 ± 1.42* | 106 |

TABLE 3.2.B

Jurkat cells co-incubated with 15 uM of the polypeptide for 38 h (%)

| Grouping | Cell survival rate (%) | Cell count (%) |
|---|---|---|
| Control | 100.00 ± 1.65 | 100.00 ± 12.75 |
| C-p | 79.02 ± 2.12 | 90.81 ± 15.84 |
| P-t | 78.04 ± 0.84* | 69.55 ± 8.35* |

TABLE 2.2.C

Jurkat cells co-incubated with 15 uM of the polypeptide for 24 + 38 h (%)

| Grouping | Cell survival rate (%) | Cell count (%) |
|---|---|---|
| Control | 100.00 ± 0.72 | 100.00 ± 0.50 |
| C-p | 98.81 ± 0.10 | 91.90 ± 4.45 |
| P-t | 69.19 ± 0.95* | 70.09 ± 18.75 |

The Second Experiment

TABLE 2.2.D

Jurkat cells co-incubated with 15 uM of the polypeptide for 38 h (%)

| Grouping | Cell survival rate (%) | Cell count (%) |
|---|---|---|
| Control | 100.00 ± 0.90 | 100.00 |
| C-p | 93.34 ± 0.95 | 92.68 |
| P-t | 74.96 ± 1.25* | 73.17 |

TABLE 2.2.E

Jurkat cells co-incubated with 15 uM of the polypeptide for 24 + 38 h (%)

| Grouping | Cell survival rate (%) | Cell count (%) |
|---|---|---|
| Control | 100.00 ± 2.65 | 100.00 |
| C-p | 96.93 ± 1.38 | 97.67 |
| P-t | 59.78 ± 0.79** | 65.12 |

(3) Thp-1 Cells Co-Incubated with the Polypeptide for 38 h/24+38 h

The First Experiment

TABLE 2.3.A

Thp-1 cells co-incubated with 10 uM of the polypeptide for 38 h (%)

| Grouping | Cell survival rate (%) | Cell count (%) |
|---|---|---|
| Control | 100.00 ± 0.84 | 100.00 |
| C-p | 100.84 ± 1.91 | 75.00 |
| P-t | 90.80 ± 3.98* | 80.56 |

TABLE 2.3.B

Thp-1 cells co-incubated with 15 uM of the polypeptide for 38 h (%)

| Grouping | Cell survival rate (%) | Cell count (%) |
|---|---|---|
| Control | 100.00 ± 4.37 | 100.00 ± 17.50 |
| C-p | 93.90 ± 1.58 | 91.43 ± 2.00 |
| P-t | 73.17 ± 2.42* | 63.17 ± 2.50 |

TABLE 2.3.C

Thp-1 cells co-incubated with 15 uM of the polypeptide for 24 + 38 h (%)

| Grouping | Cell survival rate (%) | Cell count (%) |
|---|---|---|
| Control | 100.00 ± 0.03 | 100.00 |
| C-p | 109.98 ± 1.20 | 95.00 |
| P-t | 65.15 ± 0.03** | 63.75 |

The Second Experiment

TABLE 2.3.D

Thp-1 cells co-incubated with 15 uM of the polypeptide for 38 h (%)

| Grouping | Cell survival rate (%) | Cell count (%) |
|---|---|---|
| Control | 100.00 ± 0.37 | 100.00 |
| C-p | 94.90 ± 1.59 | 91.90 |
| P-t | 78.78 ± 0.87* | 70.09 |

TABLE 2.3.E

Thp-1 cells co-incubated with 15 uM of the polypeptide for 24 + 38 h (%)

| Grouping | Cell survival rate (%) | Cell count (%) |
|---|---|---|
| Control | 100.00 ± 0.12 | 100.00 |
| C-p | 96.92 ± 1.24 | 93.37 |
| P-t | 75.35 ± 0.96* | 68.22 |

(4) Baf-3 Cells Co-Incubated with the Polypeptide for 38 h/24+38 h

The First Experiment

TABLE 2.4.A

Baf-3 cells co-incubated with 10 uM of the polypeptide for 38 h

| Grouping | Cell survival rate (%) | Cell count (%) |
|---|---|---|
| Control | 100.00 ± 6.36 | 100.00 |
| C-p | 95.72 ± 8.29 | 98.92 |
| P-t | 99.92 ± 13.28* | 99.98 |

TABLE 2.4.B

| | Baf-3 cells co-incubated with 10 uM of the polypeptide for 24 + 38 h | |
|---|---|---|
| Grouping | Cell survival rate (%) | Cell count (%) |
| Control | 100.00 ± 2.83 | 100.00 |
| C-p | 100.65 ± 3.30 | 99.90 |
| P-t | 102.28 ± 0.15* | 100.11 |

The Second Experiment

TABLE 2.4.C

| | Baf-3 cells co-incubated with 15 uM of the polypeptide for 38 h | |
|---|---|---|
| Grouping | Cell survival rate (%) | Cell count (%) |
| Control | 100.00 ± 4.62 | 100.00 |
| C-p | 99.27 ± 6.19 | 98.01 |
| P-t | 99.51 ± 8.28* | 100.41 |

TABLE 2.4.D

| | Baf-3 cells co-incubated with 15 uM of the polypeptide for 24 + 38 h | |
|---|---|---|
| Grouping | Cell survival rate (%) | Cell count (%) |
| Control | 100.00 ± 7.13 | 100.00 |
| C-p | 100.21 ± 8.10 | 100.15 |
| P-t | 101.02 ± 2.35* | 100.83 |

The leukemia subtypes represented by the aforementioned three leukemia cells have covered more than 70% of the number of leukemia patients. Through the above experiments, it can be seen that the polypeptide can obviously inhibit the proliferation of various leukemia cells, and has a positive correlation with the dosage and times of administration. Meanwhile, it has no inhibitory effect on the proliferation of normal cells.

---

What is claimed is:

1. A polypeptide having an effect of inhibiting the proliferation of leukemia cells, wherein the polypeptide consists of 37 amino acids, with the amino acid sequence of

```
                                          SEQ ID NO: 1
Lys-Glu-Ser-Met-Asp-Ala-Asn-Lys-Pro-Thr-Lys-Asn-

Leu-Pro-Leu-Lys-Lys-Ile-Pro-Cys-Lys-Thr-Ser-Ala-

Pro-Ser-Gln-Ser-Phe-Phe-Ala-Arg-Asp-Asn-Thr-Ala-

Asn.
```

2. The polypeptide according to claim 1, wherein the N-terminus of the polypeptide is connected with myristate, and enters the leukemia cells through modification with the myristate.

* * * * *